United States Patent [19]

Bergstrand et al.

[11] 4,233,303
[45] Nov. 11, 1980

[54] XANTHINE DERIVATIVES

[75] Inventors: Sten H. A. M. Bergstrand, Bjärred; Per G. Kjellin, Lund; Carl G. A. Persson, Löberöd; Lars M. Sörenby, Lund, all of Sweden

[73] Assignee: Aktiebolaget Draco, Lund, Sweden

[21] Appl. No.: 947,002

[22] Filed: Sep. 29, 1978

[30] Foreign Application Priority Data

Oct. 14, 1977 [SE] Sweden ............................ 7711581

[51] Int. Cl.$^3$ ............................................. C07D 473/08
[52] U.S. Cl. .................................... 424/253; 544/273; 544/266; 544/267
[58] Field of Search ................. 544/273, 266, 267; 424/253

[56] References Cited

U.S. PATENT DOCUMENTS 3,632,742  1/1972  Eckert ................................ 544/267
4,120,947  10/1978  Diamond ........................... 544/273

FOREIGN PATENT DOCUMENTS 2713389  10/1977  Fed. Rep. of Germany .

Primary Examiner—Nicholas S. Rizzo
Attorney, Agent, or Firm—Brumbaugh, Graves, Donohue & Raymond

[57] ABSTRACT

Compounds of the formula

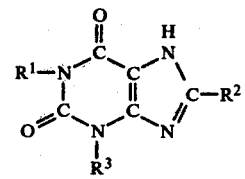

or physiologically acceptable salts thereof in which formula $R^1$ is methyl, ethyl or n-propyl, $R^2$ is methyl or n-propyl and $R^3$ is

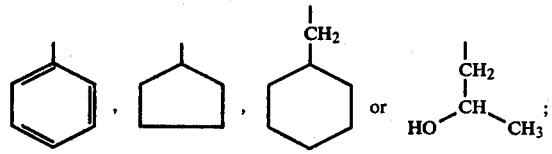

methods for the preparation thereof; intermediates useful for their preparation; pharmaceutical preparations containing at least one of these compounds; and the use thereof in the treatment of allergy and bronchial asthma.

12 Claims, No Drawings

XANTHINE DERIVATIVES

FIELD OF THE INVENTION

The present invention relates to novel, pharmacologically active compounds, methods for their preparation and their therapeutical use. The invention also relates to pharmaceutical compositions containing the compounds. More particularly, the novel compounds of the invention have antiallergic activity and are particularly valuable as antiasthmatic agents and may also be used in the therapeutic and prophylactic treatment of other allergic diseases.

BACKGROUND OF THE INVENTION

The term "allergy" means, according to Dorland's Illustrated Medical Dictionary, 24th edition, 1967, "a hypersensitive state acquired through exposure to a particular allergen, re-exposure bringing to light an altered capacity to react". As examples of different allergies may be mentioned asthma, allergic rhinitis, hay fever, and urticaria. A common feature at many types of allergic reactions in humans is an antigen-antibody reaction which leads to the release of pharmacologically active agents (=mediators) i.a. of histamine and SRS-A (=slow reacting substance of anaphylaxis). The mediators thus liberated cause bronchoconstriction, oedema, increased production of mucus, itching, etc. The reaction sequence at an allergic attack may schematically be illustrated as follows:

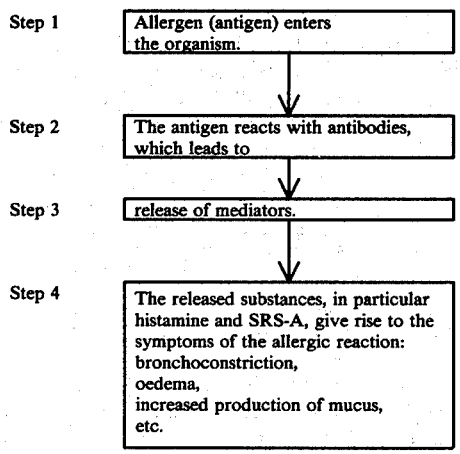

The kind of exaggerated reaction illustrated above of the organism to allergens (antigens), which may be foreign protein or other substances, is called an anaphylactic reaction.

Although in the following specification emphasis will be placed on bronchial asthma of the exogenous type, which is only one form of allergy, it will be understood that the achievements reached through the present invention will be applied also to other forms of allergy.

In the conventional treatment of asthma, symptoms appearing at step 4 are treated. In particular, the constriction of the bronchi is relieved by administering substances which relieve the bronchial spasm and thus dilate the bronchi. This treatment is, however, usually started only when the asthma attack is under way or already fully developed. It would be desirable to have access to a prophylactic method of treatment which thus could be used to prevent the very outbreak of allergic attacks. This could be achieved by inhibiting the release of mediators appearing in Step 3 in the schema above.

It has been demonstrated that the 1,3-dimethyl derivative of xanthine—theophylline—in some tests is capable of inhibiting the anaphylactic release of histamine, e.g. in basophil leucocytes and in isolated lung tissue.

The object of the present invention is to provide xanthine derivatives which consistently inhibit the allergic reaction in a dosage range where they do not produce "classical" theophylline side effects e.g. CNS-mediated effects and tachycardia. Compounds having a consistent inhibitory effect on the allergic reaction will be effective by various routes of administration as prophylactic antianaphylactic agents in the treatment of allergies including bronchial asthma, without yielding the side effects which may be noted with theophylline drugs conventionally used as bronchospasmolytic agents.

DETAILED DESCRIPTION OF THE INVENTION

It has been found according to the present invention that the compounds of the formula

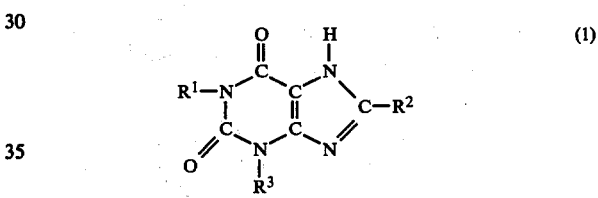

and the physiologically acceptable salts thereof, wherein $R^1$ is methyl, ethyl, or n-propyl, $R^2$ is methyl or n-propyl and $R^3$ is

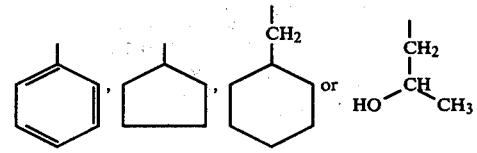

possess a pronounced antiallergic effect. This advantageous property makes the compounds of the invention valuable in the prophylactic and therapeutic treatment of various forms of allergy such as allergic rhinitis, hay fever, urbicaria, asthma, etc.

Among the compounds of the above formula are

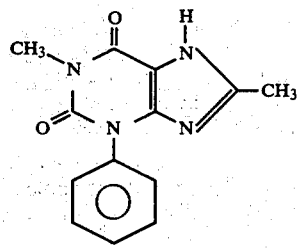

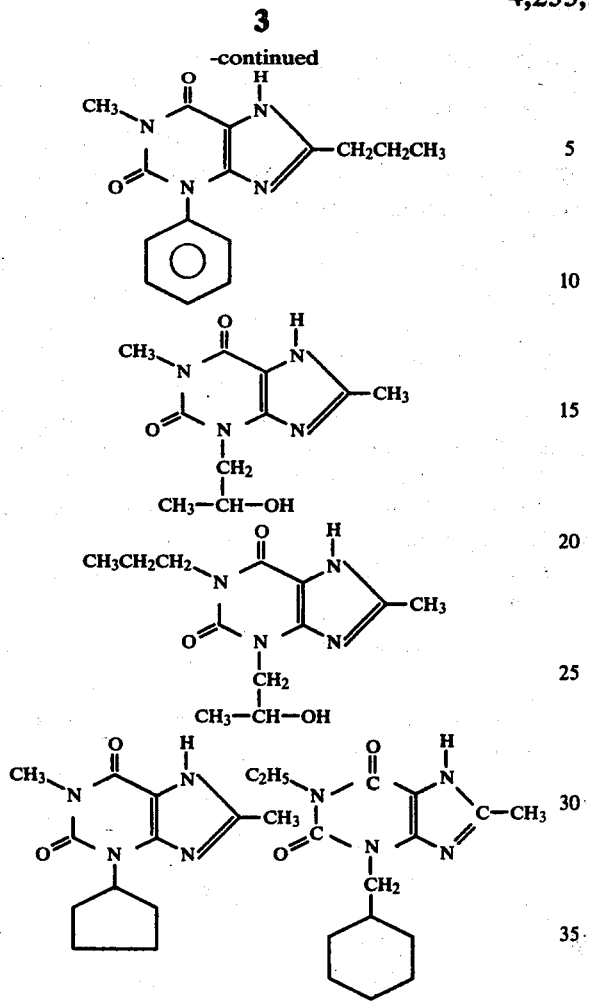

The preferred compound of the invention has the formula

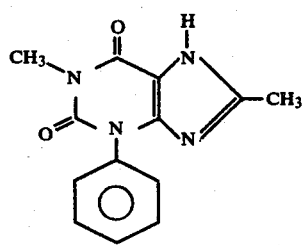

As those compounds of the invention wherein R¹ is

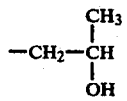

possess an asymmetric carbon atom, the invention also includes all the possible optically active forms and racemic mixtures of the compounds. The racemic mixtures may be resolves by conventional methods, for example by salt formation with an optically active acid, followed by fractional crystallization.

This invention also takes into consideration that compounds which structurally deviates from the formula (1) after administration to a living organism may be transformed therein to a compound of the formula (1) and in this structural form exerting their efforts. This consideration is a further aspect of this invention.

The present invention includes pharmaceutically acceptable salts of compounds of formula (1) with pharmaceutically acceptable bases. By the term "pharmaceutically acceptable salts" is meant salts the cations of which are relatively innocuous to the animal organism when used in therapeutic doses so that the beneficial pharmacological properties of the parent compounds of general formula (1) are not vitiated by side effects ascribable to those cations. Suitable satls include the alkali metal, e.g. sodium and potassium, and ammonium salts and salts of amines known in the art to be pharmaceutically acceptable, e.g. ethylene diamine, choline, diethanolamine, triethanolamine, octadecylamine, diethylamine, triethylamine, 1-amino-2-propanol, 2-amino-2-(hydroxymethyl)propane -1,3 - diol and 1-(3,4-dihydroxyphenyl)-2-isopropylaminoethanol.

Pharmaceutically acceptable salts may be prepared by the reaction together of stoichiometric quantities of a compound of formula (1) and the appropriate base, that is to say, a base as described immediately hereinbefore, for example at an elevated temperature, with or without an appropriate solvent, preferably followed by recrystallisation from an appropriate solvent, for example a hydroxylic solvent, e.g. water, of the salt so formed.

In clinical practice the compounds of the present invention will normally be administered orally, rectally, nasally, sublingually, by injection or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. Usually the active substance will comprise between 0.1 and 99% by weight of the preparation, for example between 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative, polyvinylpyrrolidone or gelatine and also may include lubricants such as magnesium or calcium stearate or a Carbowax ® or other polyethylene glycol waxes and compressed to form tablets or cores for dragees. In dragees are required, the cores may be coated, for example with concentrated sugar solutions which may contain gum arabic, talc and/or titanium dioxide, or alternatively with a film forming agent dissolved in easily volatile organic solvents or other suitable solvent or mixtures of organic solvents. Dyestuffs can be added to these coatings, for example, to distinguish between different contents of active substance. For the preparation of soft gelatine capsules (pearl-shaped closed capsules) consisting of gelatine and, for example, glycerol as a plasticizer, or similar closed capsules, the active substance may be admixed with a Carbowax ® or a suitable oil as e.g. sesam oil, olive oil, or arachis oil.

Hard gelatine capsules may contain granulates of the active substance with solid, pulverulent carriers such as lactose, saccharose, sorbitol, mannitol, starches (for example potato starch, corn starch or amylopectin), cellulose derivatives, polyvinylpyrrolidone or gelatine, and may also include magnesium stearate or stearic acid as lubricants.

A compound of the invention may also be formulated as a sustained action dosage form using suitable excipients. Different methods may be used for the availability control e.g. diffusion process and ion exchange. Methods using the diffusion process may be exemplified by products involving coated granules or particles, matrix imbedded drug and slightly soluble forms.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution or suspension of the active substances according to the invention, desirably in a concentration of 0.5-10%, and optionally also a stabilizing agent and/or buffer substances in aqueous solution. Dosage units of the solution may advantageously be enclosed in ampoules.

The dosage at which the active ingredients are administered may vary within a wide range and will depend on various factors such as for example the individual requirements of each patient. A suitable oral dosage range is from 10 to 1000 mg given 1-4 times a day. A suitable dosage range at parenteral administration is from 1 to 500 mg.

The pharmaceutical compositions containing the active ingredients may suitably be formulated so that they provide doses within these ranges either as single dosage units or as multiple dosage units.

The compounds of the invention can be prepared by any of the following methods.

A. Reacting a compound of the formula

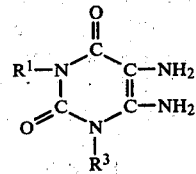

wherein $R^1$ is methyl, ethyl or n-propyl and $R^3$ is

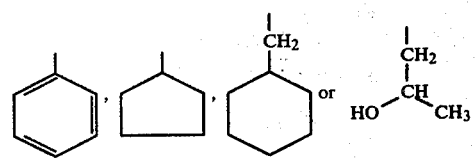

with a compound of the formula $$R^2-X$$

wherein $R^2$ is methyl or n-propyl and X is —COOH or —OC—O—CO—$R^2$ and, if necessary, submitting the obtained product to dehydration.

The dehydration may be carried out for instance by heating the reaction mixture in the absence of solvent or by heating the mixture with alkali or by boiling the mixture in a high-boiling solvent.

The starting material of this route may be prepared for example as illustrated in the reactions below, wherein the radicals $R^1$ and $R^3$ have the meaning given in this specification.

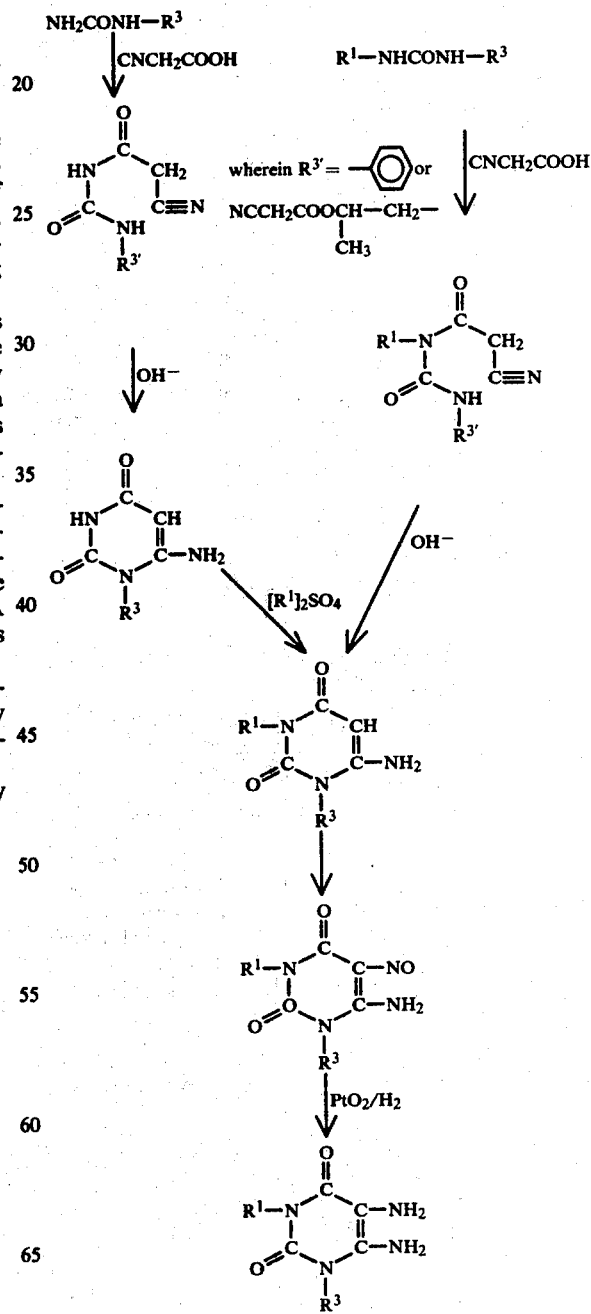

B. Reacting a compound of the formula

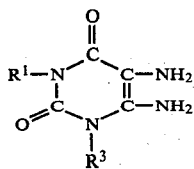

wherein $R^1$ is methyl, ethyl or n-propyl and $R^3$ is

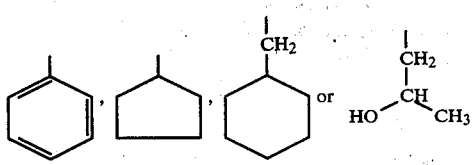

with a compound of the formula $R^2-X'$ wherein $R^2$ is methyl or n-propyl and $X'$ is —CHO or

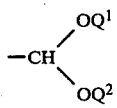

and submitting the obtained product to oxidative cyclization. $Q^1$ is hydrogen or an alkyl group with 1–3 carbon atoms and $Q^2$ is an alkyl group with 1–3 carbon atoms. Preferably $Q^1$ and $Q^2$ are ethyl or methyl.

The oxidative cyclization a variety of agents can be used, e.g. thionyl chloride, $SOCl_2$.

The following examples illustrate the invention.

EXAMPLE 1.

Preparation of 3,7-dihydro-1,8-dimethyl-3-(2-hydroxypropyl)-1H-purine-2,6-dione VIII (a) Preparation of 6-amino-1-(2-hydroxypropyl)-2,4- -(1H, 3H)-pyrimidinedione III To a solution of 328 g (3.9 mol) cyanoacetic acid and 750 ml of acetic anhydride was added 228 g (1.93 mol) of 2-hydroxypropyl- urea (I) in portions. The solution was stirred at 60°–70° C. for 1 hour. After cooling crystals were filtered off and washed with ethanol. Yield 308.8 g(II). This was stirred in 300 ml of hot water. 245 ml of 5 N NaOH was added in portions until a basic reaction. The solution was neutralized with 2 ml of 5 N HCl. After cooling, white crystals were filtered off. Yield 106.5 g (III) NMR.

(b) Preparation of 6-amino-1-(2-hydroxypyropyl)-3-methyl-2,4- -(1H, 3H)-pyrimidinedione IV To 120 ml of 5 N NaOH (0.6 mol) was added 106.5 g (0.58 mol) of 6-amino-1-(2-hydroxypropyl)-2,4-(1H, 3H)-pyrimidinedione (III) in small portions. The solution was stirred and 67 ml (0.7 mol) of dimethylsulphate was added dropwise and the temperature was not allowed to go above 40° C. After all the dimethylsulphate was added, the received suspension was heated to 60° C. and neutralized to pH 6. After cooling white crystals were filtered off and recrystallized from 100 ml of water. Yield 79 g (IV) NMR.

(c) Preparation of 6-amino-1-(2-hydroxypropyl)-3-methyl- -5-nitroso-2,4-(1H, 3H)-pyrimidinedione V To 79 g (0.4 mol) of 6-amino-1-(2-hydroxypropyl)-3-methyl- 2,4-(1H, 3H)-pyrimidinedione (IV), dissolved in 500 ml of ethanol, was added 30 g $NaNO_2$ (0.43 mol) which was dissolved in water, whereafter 36 ml conc. hydrochloric acid was added. The red crystals were dissolved through boiling and the sodium chloride was filtered off. The red filtrate was used for synthetizing 5,6-diamino-1-(2-hydroxypropyl)-3-methyl-2,4-(1H, 3H)-pyrimidinedione (VI) NMR.

(d) Preparation of 5,6-diamino-1-(2-hydroxypropyl)-3-methyl-2,4-(1H, 3H)-pyrimidinedione VI The solution from the synthesis of 6-amino-1-(2-hydroxypropyl)- 3-methyl-5-nitroso-2,4-(b 1H, 3H)-pyrimidiendione was catalytically hydrogenated in the presence of 0.3 g $PtO_2$ at room temperature and 265 kPa for 30 minutes. The catalyst was filtered off and the filtrate evaporated to 100 ml. The crystals were filtered off. Yield 63.7 g (VI).

(e) Preparation of 6-amino-3-(2-hydroxypropyl)-1-methyl-2,4-(1H, 3H)-pyrimidinedione IV To a solution of 75 g (1 mol) 1-aminopropanol-2 in 200 ml of chloroform was added 65 ml of methylisocyanate. The solution was stirred below 35° C. and then evaporated. The colourless oil of IX was used directly. This oil was added to a solution of 170 g cyanoacetic acid and 400 ml of acetic anhydride. The solution was stirred at 60°–70° C. for 2 hours and then evaporated. This yellow oil of IX was dissolved in 400 ml of hot water and 350 ml of 5 N NaOH was added to a basic reaction. After refluxing for 30 minutes the reaction mixture was neutralized and white crystals were filtered off. Yield 86 g (IV). NMR (f) Preparation of 3.7-dihydro-1,8-dimethyl-3-(2-hydroxypropyl)-1H-purine-2,6-dione VIII 16 g (0.075 mol) of 5,6-diamino-1-(2-hydroxypropyl)-3-methyl-2,4-(1H, 3H)-pyrimidinedione (VI) was refluxed in 35 ml of acetic acid for 15 minutes. To the warm solution 30 ml of chloroform was added and ether was then added slowly. The received crystals were filtered off. Yield 16 g (VII). These crystals were refluxed in 40 ml of 2 N NaOH for 30 minutes and then neutralized with 18 ml of 5 N hydrochloric acid. Crystals were filtered off and recrystallized from 50 ml of water. Yield 6.6 g (VIII). NMR.

Reaction scheme:

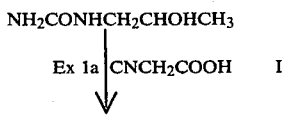

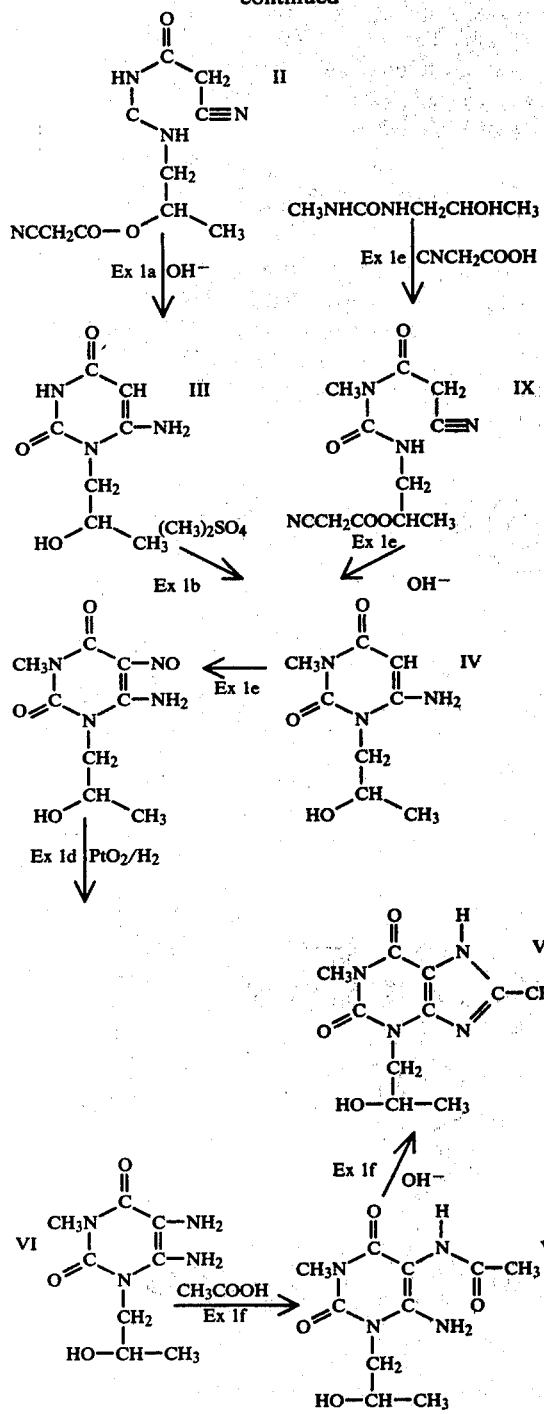

for 2 h at 60°–70° C. It was then evaporated and the residued yellow oil (X) was dissolved in 300 ml of hot water and 80 ml of 10 N NaOH was added in portions until the pH was over 7. After cooling, white crystals were filtered off. Yield 71 g (XI) NMR.

(b) Preparation of
6-amino-1-(2-hydroxypropyl)-3-propyl-5-nitroso-2,4-(1H, 3H)-pyrimidinedione XII Was performed according to the description of Example 1c.

(c) Preparation of
5,6-diamino-1-(2-hydroxypropyl)-3-propyl-2,4-(1H, 3H)-pyrimidinedione XIII Was performed according to the description of Example 1 d.

(d) Preparation of
3,7-dihydro-3-(2-hydroxypropyl)-8-methyl-1-propyl-1H-purine-2,6-dione XIV About 15 g of 5,6-diamino-1-(2-hydroxypropyl)-3-propyl-2,4-(1H, 3H)-pyrimidinedione as an oil was refluxed for one hour in 50 ml of acetic acid. The solution was evaporated and the residue was dissolved in water. Active carbon was added and filtered off. To the filtrate 25 ml of 5-N NaOH was added and the solution was refluxed for 30 minutes. Hydrochloric acid was added until acid reaction and the received crystals were filtered off and recrystallized from 200 ml of water. Yield 2.7 g. NMR.

Reaction scheme:

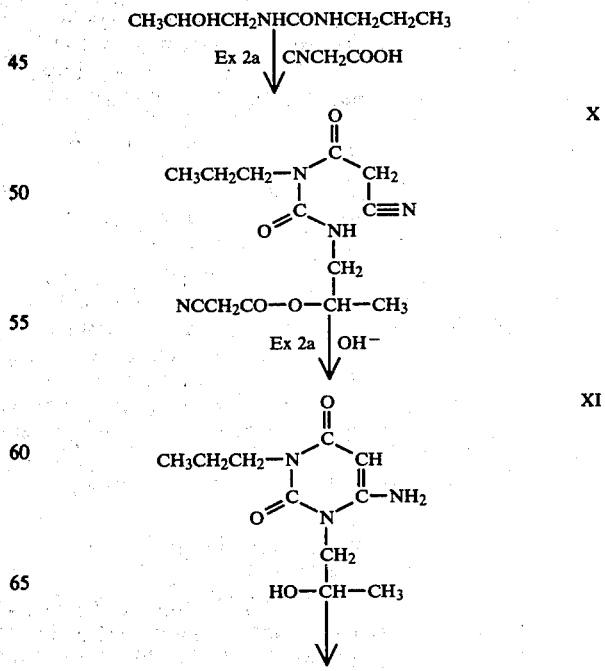

EXAMPLE 2
Preparation of
3,7-dihydro-3-(2-hydroxypropyl)-8-methyl-1-propyl-1H-purine-2,6-dione XIV (a) Preparation of
6-amino-1-(2-hydroxypropyl)-3-propyl-2,4-(1H)-pyrimidinedione XI To a solution of 85 g cyanacetic acid and 200 ml of acetic anhydride was added 80 g of 1-(2-hydroxypropyl)-3-propylurea. The reaction mixture was stirred -continued

EXAMPLE 3
Preparation of 3,7-dihydro-1,8-dimethyl-3-phenyl-1H-purine-2,6-dione XIX (a) Preparation of 6-amino-3-methyl-1-phenyl-2,4-(1H, 3H)-pyrimidinedione To a solution of 38 g (0.44 mol) of cyanacetic acid, 200 ml of acetic anhydride and 200 ml of acetic acid was added 60 g of 1-methyl-3-phenylurea. The solution was stirred at 90°–100° C. for some hours. After cooling, 65.5 g of 1-cyanoaceto-1-methyl-3-phenylurea (XV) was filtered off (mp 180° C). This was dissolved in 3 l of boiling ethanol and 10 ml of 10% soda solution was added. After cooling and filtration, the filtrate was evaporated and the crystals were washed with ethanol. Yield 46.7 g (XVI) NMR.

(b) Preparation of 6-amino-3-methyl-5-nitroso-1-phenyl-2,4-(1H, 3H)-pyrimidinedione XVII To 46.7 g of the pyrimidinedione (XVI) dissolved in 200 ml of DMSO was added 15 g NaNO₂ dissolved in 25 ml of water. The temperature of this solution was 60°. To this 18 ml of concentrated hydrochloric acid was added, whereby the temperature raised to 100° C. and the reaction mixture became deep-red. After 30 minutes, 1,5 l of water was added and the crystals were filtered off and washed with water. Yield 40.5 g (XVII). NMR.

(c) Preparation of 5,6-diamino-3-methyl-1-phenyl-2,4-(1H, 3H)-pyrimidinedione XVIII 40.5 g of 6-amino-3-methyl-5-nitroso-1-phenyl-2,4-(1H, 3H)-pyrimidinedione (XVII) in 500 ml of DMF and in the presence of 0.3 g of PtO₂ was the solution catalytically hydrogenated for 20 minutes at a pressure of 200 kPa. The reaction mixture was heated and the catalyst was filtered off. After cooling, crystals were filtered off and washed with DMF and water. Yield 21.4 g (XVIII). NMR (d) Preparation of 3,7-dihydro-1,8-dimethyl-3-phenyl-1H-purine-2,6-dione XIX A solution of 12.5 g (0.054 mol) of 5,6-diaminol-3-methyl-1-phenyl-2,4-(1H, 3H)-pyrimidinedione in 100 ml of acetic anhydride was reluxed for 5 hours. After cooling, grey crystals were filtered off and recrystallized from 300 ml of ethanol. Yield 4.0 g (XIX). NMR. Reaction scheme:

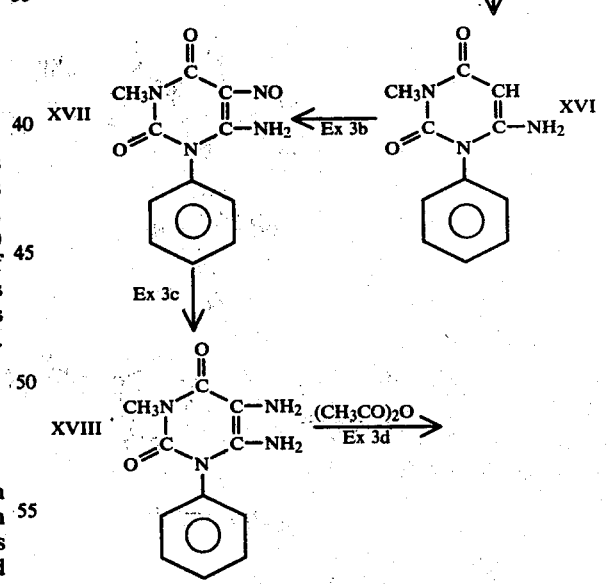

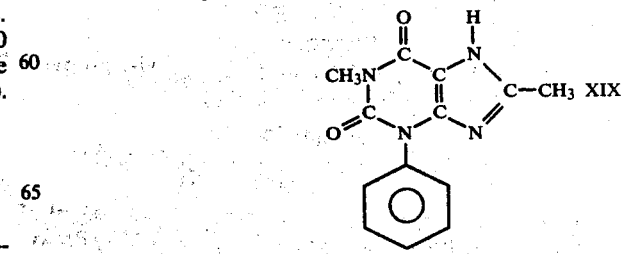

EXAMPLE 4

Preparation of 3,7-dihydro-1-methyl-3-phenyl-8-propyl-1H-purine-2,6-dione

A solution of 3 g of 5,6-diamino-3-methyl-1-phenyl-2,4-(1H, 3H)-pyrimidinedione XVIII in 25 ml of butyric anhydride was refluxed for 16 hours. After cooling, grey crystals were filtered off and recrystallized from 100 ml of ethanol. Yield 1.1 g NMR.

EXAMPLE 5

Preparation of 3-cyclopentyl-3,7-dihydro-1,8--dimethyl-1H-purine-2,6-dione XXVI (a) Preparation of 6-amino-1-cyclopentyl-3-methyl-2,4-(1H, 3H)-pyrimidinedione XXII To a solution of 47 g (0.55 mol) of cyanoacetic acid and 150 ml of acetic anhydride was added 73.1 g (0.51 mol) of 1-cyclopentyl-3-methylurea (XX). The solution was stirred at 70° C. for two hours. It was then evaporated and the residual oil (XXI) was dissolved in 400 ml of ethanol and 400 ml of water and 110 ml of 5 N NaOH was added in portions until the pH was over 7, under which the solution was boiled. It was then partly evaporated and crystals were filtered off. These crystals were a mixture of XX (~30%) and XXII (~70%) which was used for synthetizing XXII. Yield 30.8 g. NMR.

(b) Preparation of 6-amino-1-cyclopentyl-3-methyl-5-nitroso-2,4-(1H, 3H)-pyrimidionedione XXIII To 21.6 g of the pyrimidinedione (XXII) dissolved in 150 ml of ethanol was added 8 g NaNO$_2$ dissolved in 10 ml of water and 24 ml of 5 N hydrochloric acid. After 30 minutes, red crystals were filtered off. Yield 21.8 g. NMR.

(c) Preparation of 1-cyclopentyl-5,6-diamino-3-methyl-2,4-(1H3H)-pyrimidinedione XXIV A suspension of 21.8 g of the pyrimidinedione (XXIII) in 700 ml of ethanol was catalytically hydrogenated in the presence of 0.1 g PtO$_2$ for 2 h at a pressure of 265 kPa. The catalyst was filtered off and the solution was evaporated and ether was added and the crystals were filtered off. Yield 12.0 g (XXIV). NMR.

(d) Preparation of 3-cyclopentyl-3,7-dihydro-1,8-dimethyl-1H-purine-2,6-dione XXVI 5 g of the pyrimidinedione (XXIV) was refluxed in 20 ml of acetic acid for 30 minutes. 30 ml of chloroform was added and ether was then added slowly. The received crystals were filtered off. Yield 5.3 XXV. These crystals were refluxed in 15 ml of 2 N NaOH for 1 h and then neutralized with 5 N hydrochloric acid. Crystals were filtered off and recrystallized from 75 ml of ethanol. Yield 2.8 g (XXVI). NMR.

Reaction scheme:

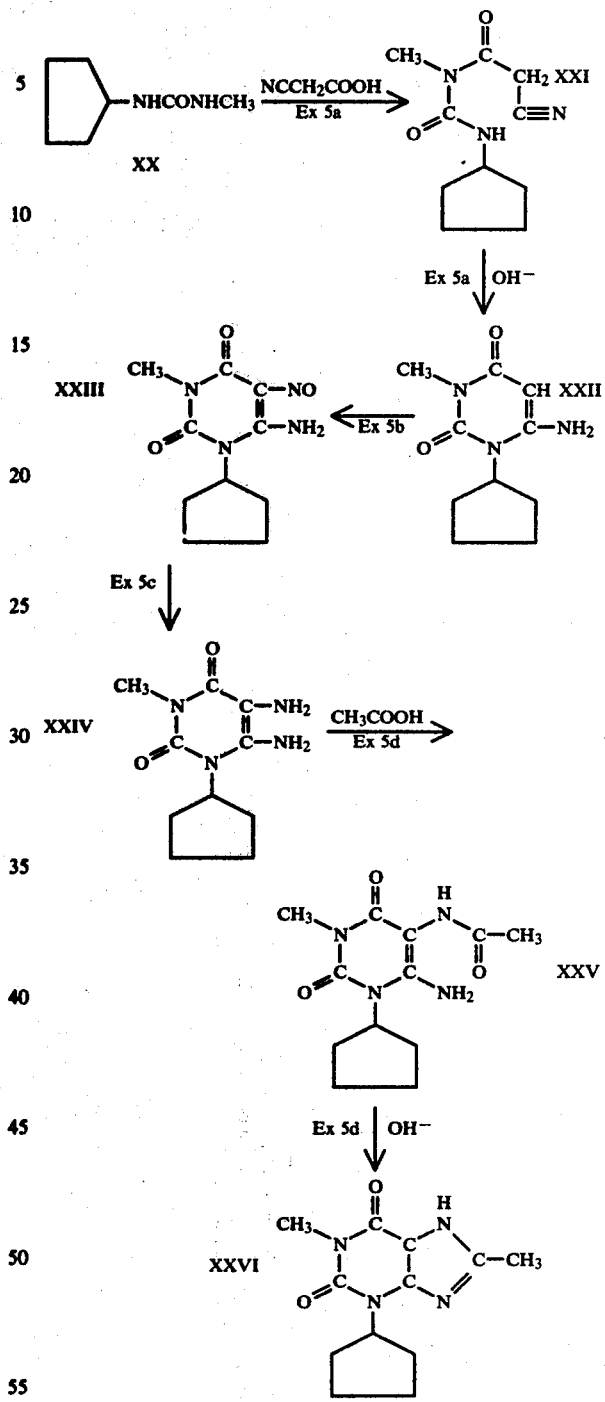

EXAMPLE 6

Preparation of 3,7-dihydro-1-dihydro-1-ethyl-8-methyl-3cyclohexylmethyl-1H-purine-2,6-dione XXXIII (a) Preparation of 6-amino-3-3-ethyl-1-cyclohexylmethyl-2,4(1H, 3H)-pyrimidinedione XXIX Was performed according to the description of Example 4a.

(b) Preparation of 6-amino-3-ethyl-1-cyclohexylmetyl-5-nitroso-2,4-(1H,3H)-pyrimidinedione XXX Was performed according to the description of Example 4 b.

(c) Preparation of 5,6-diamino-3-cyclohexylmethyl-2,4-(1H,3H)-pyrimidinedione XXXI Was performed according to the description of Example 4c.

(d) preparation of 3,7-dihydro-1-ethyl-8-methyl-3-cyclohexylmethyl-1H-purine-2,6-dione XXXIII 8 g of the pyrimidinedione (XXXI) was refluxed in 10 ml of acetic acid for 2 h. 10 ml of chloroform was added and ether was then added slowly. The received crystals were filtered off. Yield 4.0 g XXXII. These crystals were refluxed in 10 ml of 2 N NaOH for 1 h and then neutralized with 5 N hydrochlorid acid. Crystals were filtered off and recrystallized from 25 ml of ethanol. Yield 2.0 g NMR.

Reaction scheme:

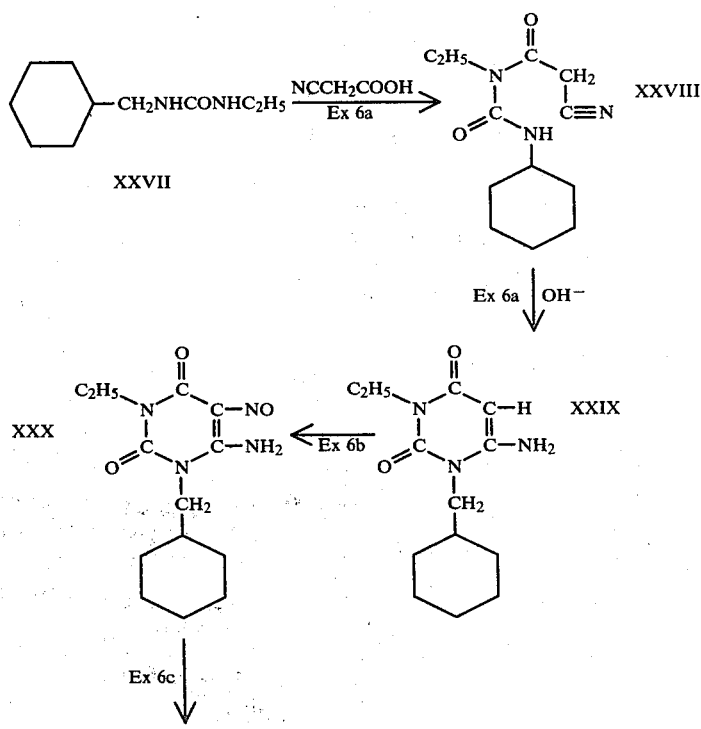

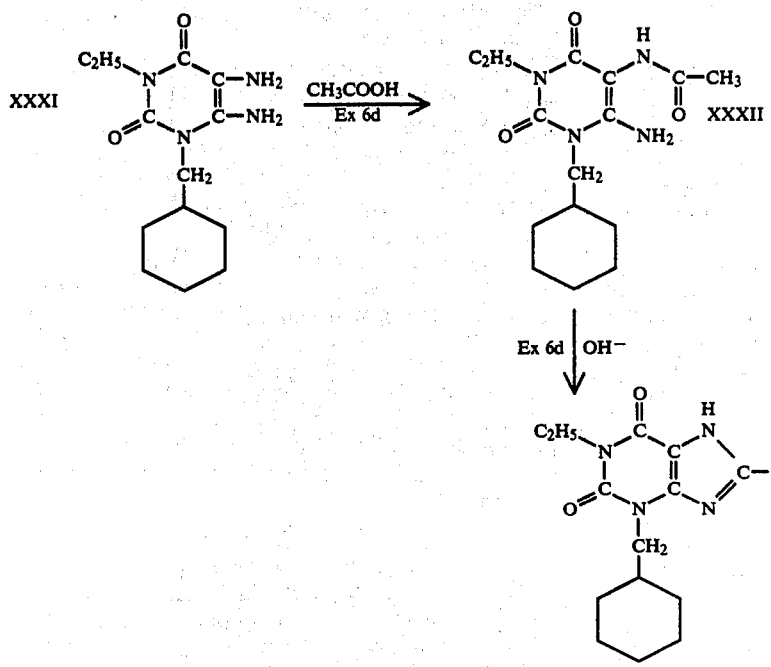

The following Examples illustrate how the compounds of the invention can be incorporated in pharmaceutical compositions.

EXAMPLE 7

Aerosol for inhalation

Active substance: 1.50 g
"Miglyol" (Registered Trade Mark): 0.20 g.
"Frigen" (Registered Trade Mark) 11/12/113/114: ad 100.0 g.

"Frigen" is used to denote the halogenated hydrocarbons. "Frigen" 114 is 1,2-dichloro-1,1,2,2-tetrafluoroethane, "Frigen" 113 is 1,1-difluoro-2,2-dichlorotrifluorotrichloroethane, "Frigen" 11 is richloromonofluoromethane and "Frigen" 12 is dichlorodifluoromethane. "Miglyol" denotes a triglyceride of saturated vegetable oils.

EXAMPLE 8

Tablets.

Each tablet contains:

| | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

EXAMPLE 9

Suppositories

Each suppository contains:
Active substance: 50.0 mg
Ascorbyl palmitate: 1.0 mg
Suppository base (Imhausen H): ad 2.000.0 mg

EXAMPLE 10

Injection solution

Active substance: 2.000 mg
Sodium hydroxide: 0.310 mg
Sodium purosulphite: 0.500 mg
Disodium edetate: 0.100 mg
Sodium chloride: 8.500 mg Sterile water for injection: ad 1.00 g

EXAMPLE 11

Sublingual tablets.

Each tablet contains:
Active substance: 20.0 mg
Lactose: 85.0 mg
Agar: 5.0 mg
Talc: 5.0 mg

PHARMACOLOGICAL TESTS

Active lung anaphylaxis in the rat

The antianaphylactic effect was tested on actively sensitized laboratory animals.

The active sensitization of the animals was achieved by injecting ovalbumin, a protein. This administration makes the animals hypersensitive to subsequent challenge of ovalbumin with bronchoconstriction as a consequence. The antianaphylactic effect of the test compounds was tested in vivo by exposing the actively sensitized animals to ovalbumin and measuring the protective effect of test substance on the intratracheal pressure.

Immunisation procedure

Rats, Spargue Dawley, 250 g, were sensibilized by 1.0 mg ovalbumin (Sigma) and 200 mg Al(OH)₃gel suspended in 1.0 ml saline. This suspension was administered subcutaneously at 2 sites (0.5 ml/site) on the abdominal side. This procedure was done with the animals lightly anesthetized by Mebumal. 18–26 days later the animals were used in the provocation experiments Provocation treatment The animal was anesthetized by i.p. injection of Mebumal, 50 mg/kg i.p. The trachea was cannulated and the animals was ventilated by a pump (Braun). The frequency of respiration was about 80 beats/min. The intratracheal pressure was measured by a Statham pressure transducer (P23AC). The normal pressure variations were 0– cm $H_2O$.

To inhibit spontaneous respiration there was need for Curare 0.8 mg/kg i.v. Alongside with the respiratory measurements the heart rate and arterial blood pressure was measured by a Statham pressure transducer connected with a. carotis. The blood pressure, pulse rate and intratracheal pressure were registered by means of a Grass polygraph.

Bronochoconstriction was induced by 5HT, 4–5 injections in v. jugularis of a standard dose. After that a single dose of ovalbumin, 5 mg, was administered. Test compound was administered 1 min before the challenging dose of ovalbumin. Because of desensitization towards the antigen (ovalbumin) this could only be administered once in each animal.

Calculation of anaphylactic bronchoconstriction

The maximum increase of the intratracheal pressure caused by ovalbumin was measured and this was expressed as the percentage increase of the intratracheal pressure. Comparisons were made between a group of control animals not treated with test compound and groups of animals treated with different doses of test compound.

Test compounds

The compounds tested in the rats were
3,7-dihydro-1,3-dimethyl-3-phenyl-1H-purine-2,6-dione XIX (with the designation D 4026).
3,7-dihydro-1,8-dimethyl-3-(2-hydroxypropyl)-1H-purine-2,6-dione VIII (with the designation D 4086).
3,7-dihydro-3-(2-hydroxypropyl)-8-methyl-1-propyl-1H-purine-2,6-dione XIV (with the designation D 4122).
3-cyclopentyl-3,7-dihydro-1,8-dimethyl-1H-purine-2,6-dione XXVI (with the designation D 4136).
3,7-dihydro-1-etyl-8-methyl-3-cyclohexylmethyl-1H-purine-2,6-dione XXXIII (with the designaton D 4139).

They were initially dissolved in 0.8 ml NaOH (0.5 M) and 9.2 ml saline. This stock solution of compound, 10 mg/ml, was diluted further with saline if necessary. Theophylline (the sodium salt) was tested in two series. The compound was dissolved in saline.

Results

Ovalbumin, 5 mg intravenously, caused a marked increase of the intratracheal pressure of the sensitized and artificially ventilated rat.

The increase was slower in onset and of longer duration than that produced with 5 HT.

The test compounds D 4026, 4086, 4122, 4136 and 4139 when administered intravenously 1 minute before ovalbumin diminished the increase of the intratracheal pressure (table I,II,III, IV and V). D 4026 showed a dose dependent inhibition of the anaphylactic bronchospasm in the concentrations 0.01–0.10 mg/kg with a maximum inhibition of about 87%. D 4139 showed inhibition in the concentrations 0.01–0.10 mg/kg with a maximum inhibition of 68%. D 4122 showed inhibition in the concentrations 0.01–1.00 mg/kg with a maximum inhibition of 79%.

Finally, theophylline and disodiumcromoglicate were tested (table VI and VII). Theophylline 0,1–2,5 mg/kg showed a partial and inconsistent protective effect on the anaphylactic bronchoconstriction in the rat revealed in two batches of animals. The same was found with disodiumcromoglicate 0,1–5 mg/kg when studied in one batch of animals.

Extrapolated dose producing 50% protection against the anaphylactic bronchospasm was calculated for the compounds tested. As can be seen from the results given in table VIII the compounds D 4026, 4122, and 4139 were most potent showing ED 50 vaues < 0.1 mg/kg. The other test compounds D 4086 and 4139 showed ED 50 values 0.10–0.27 mg/kg. The reference compounds theophylline and disodiumcromoglicate, however, showed, bell shaped curves which made it impossible to calculate ED 50 values.

Conclusion

The xanthinederivatives D 4026, 4086, 4122, 4136 and 4139 show protective effect in the actively sensitized rat against anaphylactic bronchospasm. Doses needed for this were low, 0.01–1.0 mg/kg. Theophylline did not show dosedependent protection in the dose range 0.010–2.5 mg/kg. Neither did disodiumcromoglicate in the dose range 0.1–5.0 mg/kg.

TABLE I

Increase in intratracheal pressure (+ ΔP) in active lung anaphylaxis of the rat. Mean values ± S.E.M. and number of experiments are given.

| Compound, mg/kg i.v. | | + Δ P (%) | n |
|---|---|---|---|
| control | 0 | 57 ± 10 | 8 |
| D 4026 | 0.010 | 33 ± 6 | 5 |
| D 4026 | 0.100 | 7 ± 2 | 5 |
| D 4026 | 0.500 | 9 ± 5 | 5 |

TABLE II

Increase intratracheal pressure (+ Δ P) in active lung anaphylaxis of the rat. Mean values ± S.E.M. and number of experiments are given.

| Compound, mg/kg i.v. | | + Δ P (%) | n |
|---|---|---|---|
| control | 0 | 46 ± 9 | 6 |
| D 4086 | 0.100 | 26 ± 6 | 6 |
| D 4086 | 0.250 | 14 ± 3 | 4 |
| D 4086 | 0.500 | 2 ± 1 | 4 |

TABLE III

Increase in intratracheal pressure (+ Δ P) in active lung anaphylaxis of the rat. Mean values ± S.E.M. and number of experiments are given.

| Compound, mg/kg i.v. | | +ΔP (%) | n |
|---|---|---|---|
| control | 0 | 85 ± 13 | 8 |
| D 4122 | 0.010 | 34 ± 4 | 5 |
| D 4122 | 0.100 | 23 ± 5 | 5 |
| D 4122 | 1.000 | 18 ± 4 | 5 |

Table IV

Increase in intratracheal pressure (+ Δ P) in active lung anaphylaxis of the rat. Mean values ± S.E.M. and number of experiments are given.

| Compound, mg/kg␣i.v. | | + Δ P (%) | n |
|---|---|---|---|
| Control | 0 | 81 ± 18 | 4 |
| D 4136 | 0.025 | 36 ± 4 | 4 |

Table IV-continued

Increase in intratracheal pressure (+ Δ P) in active lung anaphylaxis of the rat. Mean values ± S.E.M. and number of experiments are given.

| Compound, mg/kg i.v. | + Δ P (%) | n |
|---|---|---|
| D 4136 | 0.10 | 55 ± | 4 |
| D 4136 | 1.00 | 27 ± 4 | 4 |

Table V

Increase in intratracheal pressure (+ Δ P) in active lung anaphylaxis of the rat. Mean values ± S.E.M. and number of experiments are given.

| Compound | mg/kg i.v. | + Δ P (%) | n |
|---|---|---|---|
| control | 0 | 109 ± 17 | 4 |
| D 4139 | 0.01 | 74 ± 22 | 5 |
| D 4139 | 0.05 | 50 ± 26 | 5 |
| D 4139 | 0.10 | 35 ± 9 | 5 |

TABLE VI

Increase in intratracheal pressure (+ΔP) in active lung anaphylaxis of the rat. Mean values ± S.E.M. and number of experiments are given.

| Compound, mg/kg i.v. | +ΔP (%) | n |
|---|---|---|
| control | 0 | 70 ± 14 | 7 |
| theophylline | 0.100 | 31 ± 11 | 4 |
| theophylline | 0.500 | 18 ± 5 | 5 |
| theophylline | 2.50 | 42 ± 12 | 5 |
| control | 0 | 88 ± 12 | 11 |
| theophylline | 0.010 | 69 ± 21 | 3 |
| theophylline | 0.100 | 63 ± 17 | 3 |
| theophylline | 1.000 | 102 ± 10 | 3 |

Table VII

Increase in intratracheal pressure (+ Δ P) in active lung anaphylaxis of the rat. Mean values ± S.E.M. and number of experiments are given.

| Compound, mg/kg i.v. | | + Δ P (%) | n |
|---|---|---|---|
| Control | 0 | 46 ± 9 | 6 |
| Disodium-cromoglicate | 0.1 | 46 ± 7 | 5 |
| | 1.0 | 22 ± 8 | 4 |
| | 5.0 | 46 ± 6 | 3 |

Table VIII

Extrapolated intravenous dose for 50% protection (ED 50 mg/kg) in active lung anaphylaxis of the rat.

| Compound | ED 50, mg/kg i.v. |
|---|---|
| D 4026 | 0.016 |
| D 4086 | 0.12 |
| D 4122 | 0.010 |
| D 4136 | 0.13 |
| D 4139 | 0.04 |
| theophylline | bell-shaped curve |
| disodiumcromoglicate | bell-shaped curve |

What we claim is:
1. A compound of the formula

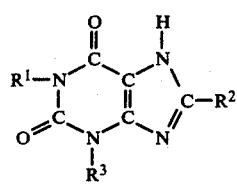

(I)

or a physiologically acceptable salt thereof, in which formula $R^1$ is methyl, ethyl or n-propyl, $R_2$ is methyl or n-propyl and $R_3$ is

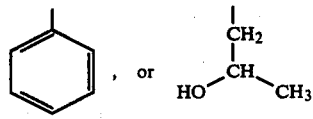

2. A compound according to claim 1 with the formula

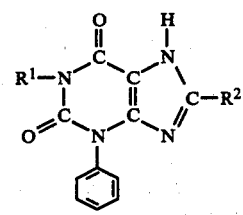

or a physiologically acceptable salt thereof, wherein $R^1$ is methyl, ethyl or n-propyl and $R_2$ is methyl or n-propyl.

3. A compound according to claim 1 or 2 with the formula

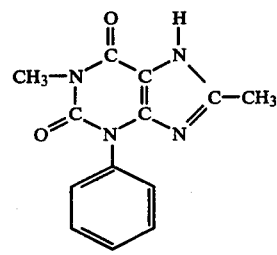

or a physiologically acceptable salt thereof.

4. A compound according to claim 1 with the formula

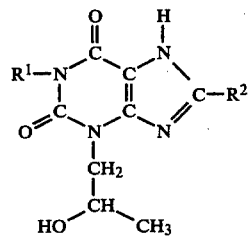

or a physiologically acceptable salt thereof, wherein $R^1$ is methyl, ethyl or n-propyl and $R_2$ is methyl or n-propyl.

5. A compound according to claim 4 in the form of a racemic mixture.

6. A compound according to claim 4 in the form of a substantially pure stereoisomer.

7. A pharmaceutical preparation comprising as active ingredient an antianaphylactic effective amount of a compound of the formula

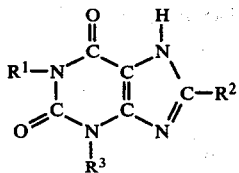

or a physiologically acceptable salt or an optical isomer thereof, in which formula $R^1$ is methyl, ethyl or n-propyl, $R^2$ is methyl or n-propyl and $R^3$ is

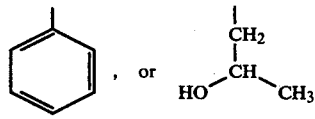

in association with a pharmaceutically acceptable carrier for use in the treatment of allergy.

8. A pharmaceutical preparation according to claim 7, comprising as active ingredient a compound according to any of claims 2, 3, 4, 5 or 6 in association with a pharmaceutically acceptable carrier.

9. A pharmaceutical preparation according to any of claims 7 or 8 in dosage unit form.

10. A method for the treatment of allergy in mammals, including man, characterized in administration to a host in need of such treatment of an effective amount of a compound of the formula

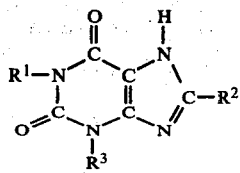

or a physiologically acceptable salt or an optical isomer thereof, in which formula $R^1$ is methyl, ethyl or n-propyl, $R^2$ is methyl or n-propyl and $R^3$ is

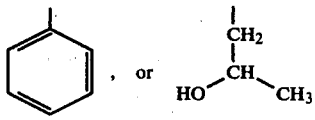

11. A method for the treatment of allergy according to claim 10, characterized in administration to a host in need of such treatment of an effective amount of a compound according to any of claims 2, 3, 4, 5 or 6.

12. A method for the treatment of bronchial asthma, characterized in administration to a host in need of such treatment of an effective amount of a compound according to any of claims 1, 2, 3, 4, 5 or 6.

* * * * *

UNITED STATES PATENT AND TRADEMARK OFFICE
CERTIFICATE OF CORRECTION

PATENT NO. : 4,233,303

DATED : November 11, 1980

INVENTOR(S) : Sten H. A. M. Bergstrand, et al.

It is certified that error appears in the above—identified patent and that said Letters Patent is hereby corrected as shown below:

Col. 4, line 55, "In" should read --If--;

Col. 6, lines 52-57, correct formula to read as follows:

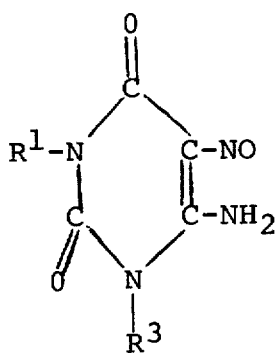

Col. 8, line 23, "(b 1H, 3H)" should read --(1H, 3H)--;

Col. 9, line 65, "1H)" should read --1H, 3H)--;

UNITED STATES PATENT AND TRADEMARK OFFICE
CERTIFICATE OF CORRECTION

PATENT NO. : 4,233,303
DATED : November 11, 1980
INVENTOR(S) : Sten H. A. M. Bergstrand, et al.

It is certified that error appears in the above—identified patent and that said Letters Patent is hereby corrected as shown below:

Col. 12, line 11, "XTX" should read --XIX--;

Col. 13, line 36, "pyrimidione-dione" should read --pyrimidinedione--;

Col. 16, line 49, correct formula XXVII to read as follows:

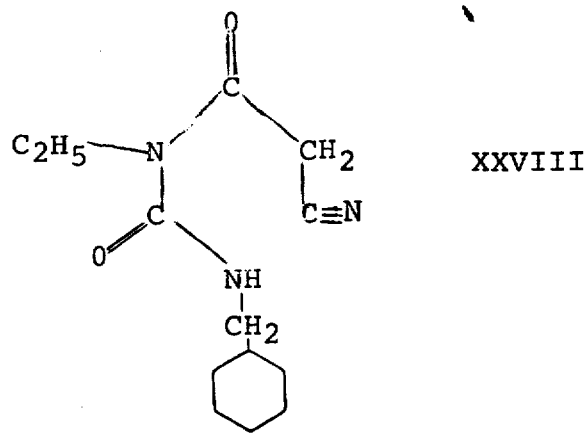

XXVIII

Col. 17, line 44, "richloromono-" should read --trichloromono-;

Col. 18, line 64, "Spargue" should read --Sprague--;

Col. 19, line 11, "0- cm" should read --0-10 cm--;

UNITED STATES PATENT AND TRADEMARK OFFICE
CERTIFICATE OF CORRECTION

PATENT NO. : 4,233,303

DATED : November 11, 1980

INVENTOR(S) : Sten H. A. M. Bergstrand, et al.

It is certified that error appears in the above—identified patent and that said Letters Patent is hereby corrected as shown below:

Col. 20, line 66, "mg/kg l.v." should read --mg/kg i.v.--;

Col. 21, line 5, "mg/kg l.v." should read --mg/kg i.v.--;

Signed and Sealed this

Twenty-seventh Day of October 1981

[SEAL]

Attest:

GERALD J. MOSSINGHOFF

*Attesting Officer*  *Commissioner of Patents and Trademarks*